United States Patent [19]

Nadeau et al.

[11] Patent Number: 5,811,269

[45] Date of Patent: Sep. 22, 1998

[54] DETECTION OF MYCOBACTERIA BY MULTIPLEX NUCLEIC ACID AMPLIFICATION

[75] Inventors: James G. Nadeau, Chapel Hill; Cheryl H. Dean, Raleigh; James L. Schram, Knightdale; Deborah R. Howard; Margaret S. Dey, both of Durham; David J. Wright, Chapel Hill, all of N.C.

[73] Assignee: Becton, Dickinson and Company, Franklin Lakes, N.J.

[21] Appl. No.: 640,378

[22] Filed: Apr. 30, 1996

[51] Int. Cl.⁶ .............................. C12P 19/34; C07H 21/04
[52] U.S. Cl. .................. 435/91.1; 435/91.2; 536/22.1; 536/24.32
[58] Field of Search ................ 536/22.1, 24.32; 435/91.2, 91.1

[56] References Cited

U.S. PATENT DOCUMENTS

| | | | |
|---|---|---|---|
| 5,422,252 | 6/1995 | Walker et al. | 435/91.2 |
| 5,470,723 | 11/1995 | Walker | 435/91.2 |

FOREIGN PATENT DOCUMENTS

| | | | |
|---|---|---|---|
| 0 364 255 | 4/1990 | European Pat. Off. | C12Q 1/68 |

OTHER PUBLICATIONS

Stackebrandt et al. Evidence of phylogenetic heterogeneity within the genus rhodococcus: revival of the genus gordona (tsukamura), J. Gen. Appl. Microbiol., vol. 34, pp. 341–348, 1988.

*Primary Examiner*—Kenneth R. Horlick
*Assistant Examiner*—Joyce Tung
*Attorney, Agent, or Firm*—Donna R. Fugit

[57] ABSTRACT

Primers and methods for adapter-mediated multiplex amplification of the IS6110 insertion element of the *Mycobacterium tuberculosis* (M.tb) complex and a 16S rDNA target common to essentially all mycobacteria are described. In certain embodiments, the primers are optimized for efficient multiplex amplification in thermophilic SDA. The multiplex Strand Displacement Amplification methods of the invention are capable, in a single amplification reaction, of simultaneously identifying *M. tuberculosis* and providing a screen for substantially all of the clinically relevant species of mycobacteria. Also disclosed are internal control sequences designed for coamplification with the two targets, allowing assessment of amplification efficiency and/or quantitation of the targets.

19 Claims, No Drawings

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
       ( A ) LENGTH: 43 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:1:

CGATTCCGCT CCACACTTCT CGGGAGAGTT TGTCGCGTTG TTC       43

( 2 ) INFORMATION FOR SEQ ID NO:2:

( i ) SEQUENCE CHARACTERISTICS:
       ( A ) LENGTH: 40 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2:

ACCGCATCGA ATGCATGTCT CGGGTAAGGC GTACTCGACC       40

( 2 ) INFORMATION FOR SEQ ID NO:3:

( i ) SEQUENCE CHARACTERISTICS:
       ( A ) LENGTH: 29 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:3:

AAGGCGTACT CGACCGCATG CTCACAGTT       29

( 2 ) INFORMATION FOR SEQ ID NO:4:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:4:

AAGGCGTACT CGACCGCATG CTCACAGTTA       30

( 2 ) INFORMATION FOR SEQ ID NO:5:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:5:

AAGGCGTACT CGACCGCACG CTCACAGTTA       30

( 2 ) INFORMATION FOR SEQ ID NO:6:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:6:

TTTGTCGCGT TGTTCGTACT GAGATCCCCT 30

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTTTGTCGCG TTGTTCTGTG TACTGAGATC CCCT 34

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGGAATTACT GGGCGT 16

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGTCTGCCCG TATCG 15

( 2 ) INFORMATION FOR SEQ ID NO:10:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGGACCCGCC AAC 13

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CGCTGAACCG GAT 13

( 2 ) INFORMATION FOR SEQ ID NO:12:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AAGGCGTACT CGACCAGCGA CGATGTCTGA GGCAACTAGC AAAGCTGAAC AACGCGACAA    60

AC                                                                 62
```

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
ACTGTGAGCA TGCGGT                                                  16
```

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAATCTCACG GCTTA                                                   15
```

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
CCTGAAAGAC GTTAT                                                   15
```

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
CCACCATACG GATAGT                                                  16
```

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GCTTTGCTAG TTGCC                                                   15
```

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCAGACATCG TCGCT 15

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:19:

CGATTCCGCT CCAGACTTCT CGGGTGTACT GAGATCCCCT 40

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:20:

GTGTACGAGA TCCCCTGACG CACGCTCACA GTTA 34

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:21:

GTTTGTCGCG TTGTTCAGAA GGTGTACTCG ACC 33

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:22:

ACTGTGAGCG TGCGTCA 17

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:23:

TTTGTCGCGT TGTTCTGTGT ACTGAGATCC CCT 33

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:24:

GTTTGTCGCG TTGTTCTGTG TACTGAGATC CCTAT 36

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:25:

GTTTGTCGCG TTGTTCTGTA CTGAGATCCC CTAT    34

(2) INFORMATION FOR SEQ ID NO:26:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:26:

GTGTACTGAG ATCCCCTAGC GACGATGTCT GAGGCAACTA GCAAAGCTGA ACAACGCGAC    60

AAAC    64

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:27:

AAGGCGTACT CGACCAGCAT GCTCACAGTT AAG    33

DETECTION OF MYCOBACTERIA BY MULTIPLEX NUCLEIC ACID AMPLIFICATION

FIELD OF THE INVENTION

The present invention relates to nucleic acid amplification, including detection and/or identification of microorganisms using nucleic acid amplification.

BACKGROUND OF THE INVENTION

The mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M kansasii, M microti, M. scrofulaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. Many of these new cases are related to the AIDS epidemic, which provides an immune compromised population which is particularly susceptible to infection by mycobacteria. Other mycobacterial infections are also increasing as a result of the increase in available immune compromised patients. *Mycobacterium avium, Mycobacterium kansasii* and other non-tuberculosis mycobacteria are found as opportunistic pathogens in HIV infected and other immune compromised patients.

At the present time the diagnosis of mycobacterial infections is primarily dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing mycobacterial infections to less than a week, preferably to about one day. Oligonucleotide probe based assays such as Southern hybridizations or dot blots are capable of returning a rapid result (i.e., in one day or less). Assays based on amplification of nucleic acids may provide even more rapid results, often within hours. For diagnosis of mycobacterial infections such methods require development of oligonucleotide probes or primers which are specific for the genus *Mycobacterium* or specific for a particular species of mycobacteria if specific identification of the organism is desired.

However, diagnosis and screening for specific nucleic acids using nucleic acid amplification techniques have generally been limited by the necessity of amplifying a single target sequence at a time. In instances where any of multiple possible nucleic acid sequences may be present (e.g., infectious disease diagnosis), performing multiple separate assays by this procedure is cumbersome and time-consuming. An improvement on the PCR which reportedly allows simultaneous amplification of multiple target sequences is described in published European Patent Application No. 0 364 255. This is referred to as multiplex DNA amplification. In this method, multiple pairs of primers are added to the nucleic acid containing the target sequences. Each primer pair hybridizes to a different selected target sequence, which is subsequently amplified in a temperature-cycling reaction similar to PCR. Multiplex amplification has also been developed for SDA. This method is referred to as adapter-mediated multiplexing, in which adapter sequences are appended to the ends of target sequences by means of adapter primers in a series of extension and strand displacement steps. These processes are described in U.S. Pat. No. 5,422,252 and in U.S. Pat. No. 5,470,723 (both incorporated by reference). In one embodiment, one of the two target sequences to be amplified is M.tb complex-specific (e.g., IS6110) and the other target sequence is common to essentially all species of mycobacteria (e.g., the 16S rRNA gene, "16S rDNA"). One end of each target strand is modified by appending to it a sequence substantially identical to a terminal segment of the other target. The other end of each target strand does not have an adapter sequence added and retains its original complementarity to one member of the amplification primer pair. The resulting adapter-modified targets can both be amplified by a single pair of amplification primers, one member of the pair being complementary to one of the two original target sequences and the other member of the pair being complementary to the other of the two original target sequences. Hybridization and extension of the amplification primers on each adapter-modified target results in a fragment with a nicking enzyme recognition site at each end. Both fragments are amplifiable by SDA using a single pair of amplification primers.

In most cases, nucleic acid amplification techniques have been used to produce qualitative results in diagnostic assays. However, there has been great interest in developing methods for nucleic acid amplification which are not only capable of detecting the presence or absence of a target sequence, but which can also quantitate the amount of target sequence initially present. Internal control sequences have been used in the PCR in an attempt to produce such quantitative results and to detect inhibition of amplification (i.e., false negatives). See, for example, WO 93/02215 and WO 92/11273. In the PCR, the amplified target and control sequences may distinguished by different fragment lengths, as the rate of the PCR is known to be relatively unaffected by the length of the target. Internal control sequences for SDA and other isothermal amplification reactions are described in U.S. Pat. No. 5,457,027 (hereby incorporated by reference).

The following terms are defined herein as follows:

An amplification primer is a primer for amplification of a target sequence by extension of the primer after hybridization to the target sequence. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *NucL. Acids Res.* 20:1691–1696). The about 10–25 nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The sequence of the tail is generally not critical and can be routinely selected and modified to obtain the desired $T_m$ for hybridization. As the target binding sequence is the portion of a primer which determines its target-specificity, for amplification methods which do not require specialized sequences at the ends of the target the amplification primer generally consists essentially of only the target binding sequence. For amplification methods other than SDA which require specialized sequences appended to the target (e.g., an RNA polymerase promoter for 3SR, NASBA or transcription based amplification), the required specialized sequence may be linked to the target binding sequence using routine methods for preparation of oligonucletoides without altering the hybridization specificity of the primer.

An adapter primer is an oligonucleotide which has a sequence of about 10–25 nucleotides at its 3' end (the target binding sequence) which hybridizes to the target sequence. The target binding sequence also confers target specificity on the adapter primer. At the 5' end of the adapter primer is an adapter sequence which is also about 10–25 nucleotides in length. The adapter sequence may be a sequence which is substantially identical to the 3' end (i.e., the target binding sequence) of one of the amplification primers or it may be any defined sequence for which amplification primers with complementary target binding sequences can be prepared. Adapter primers do not function as amplification primers in SDA, as they contain no nickable restriction endonuclease recognition site.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified and its complementary second strand (prior to addition of adapter sequences), either strand of an adapter-modified copy of the original sequence as described herein, and either strand of a copy of the original sequence which is an intermediate product of the reactions in which adapter sequences are appended to the original sequence.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term assay probe refers to any of the oligonucleotides used in the detection or identification portion of an assay. For example, in the present invention, assay probes are used for genus- or species-specific detection or identification of mycobacteria. Detector probes and capture probes are examples of assay probes.

The assay region or assay region sequence is the portion of a target sequence, or other nucleic acid, to which an assay probe hybridizes.

The term species-specific refers to detection, amplification or oligonucleotide hybridization in a species of organism or a group of related species without substantial detection, amplification or oligonucleotide hybridization in other species of the same genus or species of a different genus. Genus-specific refers to detection, amplification or oligonucleotide hybridization in the majority of the species of a genus, without substantial detection, amplification or oligonucleotide hybridization in the species of a different genus.

Identical sequences will hybridize to the same complementary nucleotide sequence. Substantially identical sequences are sufficiently similar in their nucleotide sequence that they also hybridize to the same nucleotide sequence. The adapter sequence and the amplification primer target binding sequence in an adapter primer/amplification primer pair represent segments of contiguous target sequence. An adapter primer containing an adapter sequence which is substantially identical to the target binding sequence of an amplification primer may include more or less contiguous target sequence than the amplification primer target binding sequence, or it may contain one or more single nucleotide differences. However, these minor differences between the target binding sequence of the amplification primer and the adapter sequence of the adapter primer do not prevent hybridization of the amplification primer to the complement of the adapter sequence in the adapter-modified target, and they therefore do not significantly inhibit the amplification reaction.

SUMMARY OF THE INVENTION

The present invention provides primers for adapter-mediated multiplex amplification of the IS6110 insertion element of the *Mycobacterium tuberculosis* (M.tb) complex and the 16S ribosomal RNA gene (16S rDNA) of mycobacteria. These primers are useful for detecting and/or identifying species of the *M tuberculosis* complex and other clinically relevant mycobacteria in a single nucleic acid amplification reaction. The primers are particularly well suited for use with thermophilic Strand Displacement Amplification (tSDA).

In one embodiment, the amplification reaction further includes an internal control sequence. This internal control sequence is co-amplified with the two target sequences in a multiplex amplification protocol employing a single pair of amplification primers for simultaneous amplification of the IS6110, 16S and internal control targets (triplex amplification). In this embodiment, a single amplification reaction provides means for quantitating target or detecting inhibition of the amplification reaction and detecting or identifying target sequences associated with clinically relevant mycobacteria.

DETAILED DESCRIPTION OF THE INVENTION

The present invention provides methods for simultaneous amplification of multiple target sequences by sequence specific hybridization of primers, particularly by tSDA (multiplex tSDA). The methods use a single pair of amplification primers to coamplify the multiple target sequences. This is accomplished by appending a defined adapter sequence to the targets and amplifying by primer extension in a process referred to herein as "adapter-mediated multiplexing."

The complete nucleotide sequence of the IS6110 insertion element has been described by Thierry, et al. (1990. *Nucleic Acids Res.* 18, 188). The methods of the invention provide primers for amplification of a target sequence within the IS6110 insertion element which is present in the species of the *M. tuberculosis* (M.tb) complex (*M. tuberculosis, M. bovis, M. bovis BCG, M. afticanum* and *M. microti*). The primers amplify a segment of IS6110 from nucleotides 970–1025. As the target binding sequences of the amplification primer and the adapter primer for the IS6110 target confer species-specificity for the M.tb complex, it is the adapter modification reaction which is species-specific. After species-specific adapter modification of the IS6110 target, it is amplified by the same pair of amplification primers as the adapter-modified 16S rDNA (genus-specific) target.

Alignment of the 16S ribosomal genes of various species of mycobacteria was used to design genus-specific primers for amplification of a target present in substantially all of the clinically relevant species of mycobacteria but absent in non-mycobacterial species. As shown by G. T. Walker, et al. (1994. *NucL Acids Res.* 22, 2670–2677) the selected *M. tuberculosis* sequence at nucleotide positions 507–603 is identical to the sequences in *M. bovis, M. bovis BCG, M. avium, M. intracellulare, M. kansasii, M. gastri, M. paratuberculosis, M. malmoense, M. szulgai, M. gordonae, M. leprae, M. ulcerans, M. asiaticum* and *M. scrofulaceum*. For some species in the sequence database, an undetermined nucleotide is listed at position 587 or 588. *M. terrae, M. chelonae, M. fortuitum* and our strain of *M. marinum*vary from this common sequence at three nucleotide positions. The sequence of our strain of *M. marinum* was unexpected, as the GENBANK sequence for this organism was reportedly identical to *M. bovis,* not *M. terrae, M. flavescens, M. xenopi* and *M. genavense* exhibit more extensive sequence variance. This target sequence diverges significantly from the M.tb sequence in organisms which are otherwise generally similar to mycobacteria. In spite of the sequence variability among mycobacteria, however, it was found that the primers designed to amplify a segment from nucleotides 539–587 specifically amplified the target in the clinically relevant genera of mycobacteria but not in closely related non-mycobacterial species. As the target binding sequences of the amplification primer and the adapter primer for the 16S rDNA target confer Mycobacterium genus-specificity, it is the adapter modification reaction which is genus-specific. After genus-specific adapter modification of the 16S rDNA target, it is amplified by the same pair of amplification primers as the adapter-modified IS6110 (species -specific) target.

The amplification and adapter primers of the invention are employed in multiplex SDA to simultaneously amplify an IS6110 target sequence indicative of a species of the M.tb complex and a 16S rDNA target sequence indicative of a species of the genus *Mycobacterium.*Detection of IS6110 and 16S amplicons is indicative of the presence of an *M. tuberculosis*complex organism in the sample. Detection of only 16S targets indicates the presence of non -M.tb complex mycobacteria. The amplification and adapter primers may be employed in thermophilic SDA, but may also be used in conventional, lower temperature SDA reactions. As described in U.S. Pat. No. 5,422,252, two of the four amplification primers normally required for co-amplification of two different targets are replaced in multiplex SDA with adapter primers which append one end of the first target to one end of the second target and vice versa. Following the species- and genus-specific adapter modification reaction, both targets may be amplified by a single pair of amplification primers (each directed to one end of each of the original targets), reducing the number of amplification primers required from four to two. Reducing the number of amplification primers reduces background amplification and improves the yield of amplified target. When amplification is performed at the higher reaction temperatures of tSDA, the primers of the invention allow the two targets to be detected about 4-fold faster and with about 10-fold greater sensitivity than conventional multiplex SDA using the amplification and adapter primers described in U.S. Pat. No. 5,470,723.

Certain embodiments of the primers and probes of the invention are listed in Table I. The target binding sequences of amplification primers and adapter primers are italicized. The restriction endonuclease recognition sites of amplification primers are bolded.

TABLE I

Multiplex System 1

Amplification Primers

SEQ ID NO: 1 (GS1.3 or GS1.3.B; 16S rDNA amplification primer)
CGATTCCGCTCCACACTTCTCGGGAGA*GTTTGTCGCGTTGTTC*
SEQ ID NO: 2 (Bis-S1.1; IS6110 amplification primer)
ACCGCATCGAATGCATGTCTCGGGT*AAGGCGTACTCGACC*

Alternative 16S rDNA Adapter Primers

SEQ ID NO: 3 (AG1A; 16S rDNA adapter primer)
AAGGCGTACTCGA*CCGCATGCTCACAGTT*
SEQ ID NO: 4 (AG1B; 16S rDNA adapter primer)
AAGGCGTACTCGA*CCGCATGCTCACAGTTA*
SEQ ID NO: 5 (PAS247; 16S rDNA adapter primer)
AAGGCGTACTCGA*CCGCACGCTCACAGTTA*
SEQ ID NO: 27 (AG1E; 16S rDNA adapter primer)
AAGGCGTACTCGACCA*GCATGCTCACAGTTAAG*

Alternative IS6110 Adapter Primers

SEQ ID NO: 6 (Bso-G Atb1; IS6110 adapter primer)
TTTGTCGCGTTGTTC*GTACTGAGATCCCCT*
SEQ ID NO: 7 (G1T2A; IS6110 adapter primer)
GTTTGTCGCGTTGTTC*TGTGTACTGAGATCCCCT*
SEQ ID NO: 23 (G1T2B; IS6110 adapter primer)
TTTGTCGCGTTGTTC*TGTGTACTGAGATCCCCT*
SEQ ID NO: 24 (G1T2C; IS6110 adapter primer)
GTTTGTCGCGTTGTTC*TGTGTACTGAGATCCCCTAT*
SEQ ID NO: 25 (G1T2D; IS6110 adapter primer)
GTTTGTCGCGTTGTTC*TGTACTGAGATCCCCTAT*

Bumper Primers

SEQ ID NO: 8 (Bso-G Bg1; 16S rDNA bumper primer)
CGGAATTACTGGGCGT
SEQ ID NO: 9 (Bso-G Bg2; 16S rDNA bumper primer)

TABLE I-continued AGTCTGCCCGTATCG
SEQ ID NO: 10 (Mtb 37; IS6110 bumper primer)
TGGACCCGCCAAC
SEQ ID NO: 11 (Mtb 48; IS6110 bumper primer)
CGCTGAACCGGAT Detection of System 1 Amplification SEQ ID NO: 12: (tSig1; internal control sequence)
AAGGCGTACTCGACCAGCGACGATGTCTGAGGCAACTAGCAAAGCTGAAC
AACGCGACAAAC
SEQ ID NO: 17 (capture probe for SEQ ID NO: 12)
GCTTTGCTAGTTGCC
SEQ ID NO: 18: (detector probe for SEQ ID NO: 12)
TCAGACATCGTCGCT
SEQ ID NO: 13 (TG-01B3; 16S rDNA capture probe)
ACTGTGAGCATGCGGT
SEQ ID NO: 14 (16S rDNA detector probe)
AAATCTCACGGCTTA
SEQ ID NO: 15 (IS6110 capture probe)
CCTGAAAGACGTTAT
SEQ ID NO: 16 (IS6110 detector probe)
CCACCATACGGATAGT Multiplex System 2

SEQ ID NO: 1 (16S rDNA amplification primer)
SEQ ID NO: 19 (Bis-S2.2; IS6110 amplification primer)
CGATTCCGCTCCAGACTTCTCGGG*TGTACTGAGATCCCCT*
SEQ ID NO: 20 (T2G2A; 16S rDNA adapter primer)
GTGTACGAGATCCCCTGA*CGCACGCTCACAGTTA*
SEQ ID NO: 21 (G1T1A; IS6110 adapter primer)
GTTTGTCGCGTTGTT*CAGAAGGTGTACTCGACC*
SEQ ID NOs: 8, 9, 10 and 11 (Bumper primers)

Detection of System 2 Amplification

SEQ ID NO: 22 (GCAP-2; 16S rDNA capture probe)
ACTGTGAGCGTGCGTCA
SEQ ID NO: 26 (tSig2; internal control sequence)
GTGTACTGAGATCCCCTAGCGACGATGTCTGAGGCAACTAGCAAAGCTGAA
CAACGCGACAAAC Remaining Assay Probes as Described in Example 2

Capture and detector probes SEQ ID NO:17 and SEQ ID NO:18 may be substituted in Multiplex System 2 for detection of the internal control sequence. Similarly, SEQ ID NO:14 may be substituted in Multiplex System 2 as the 16S rDNA detector probe and SEQ ID NO:15 and SEQ ID NO:16 may be substituted in Multiplex System 2 as the IS6110 capture and detector probes. Additional assay probes may be routinely designed based on the sequence between the primer binding sites in the various targets. These sequences are shown above foro the internal controls, and in Thierry, et al. and Walker, et al. (1994).

It will also be apparent to one skilled in the art that the target binding sequences of the amplification and adapter primers shown in Table I may be reversed without altering hybridization specificity (compare System 1 and System 2 primer sequences). That is, the target binding sequences of the various IS6110 adapter primers in System 1 or System 2 may be used as the target binding sequence of an IS6110 amplification primer which is then paired with an adapter primer comprising the target binding sequence of the IS6110 amplification primer shown for that System. Similarly, the 16S rDNA adapter and amplification primer target binding sequences may be reversed to produce alternative adapter/amplification primer pairs according to the invention. If an internal control sequence is desired, the termini would then be altered accordingly to allow amplification primer binding. For example, if target binding sequences in the primers are reversed, SEQ ID NO:26 would be an appropriate internal control sequence for use in System 1 and SEQ ID NO:12 would be an appropriate internal control sequence for use in System 2.

The multiplex amplification systems of the invention employ one 16S rDNA adapter primer and one IS6110 adapter primer. Table I lists several useful alternatives for each of these adapter primers in Multiplex System 1. SEQ ID NO:3 and SEQ ID NO:4 have been found to perform most efficiently in Multiplex System 1 for SDA. In contrast, Multiplex System 1 employing SEQ ID NO:5 results in amplification product yields about 10-fold lower than when SEQ ID NO:3 or SEQ ID NO:4 is the 16S rDNA adapter primer. SEQ ID NO:5 differs from SEQ ID NO:3 and SEQ ID NO:4 by only a single nucleotide (underlined in Table I). However, the sequence difference in SEQ ID NO:5 results in a perfect match when this primer hybridizes to the 16S rDNA target, whereas the sequences of SEQ ID NO:3 and SEQ ID NO:4 contain a single mismatch with the target at this position. While all three of these adapter primers function in the methods of the invention, it was unexpected that the adapter primer with perfect complementarity to the target would be less efficient than the two with lesser complementarity.

Optionally, the adapter-mediated multiplex SDA reaction may include an internal control sequence as described in U.S. Pat. No. 5,457,027. Each end of the internal control sequence is designed to hybridize to one of the amplification primers (i.e., one end representing each of the two targets) so that the internal control sequence can be coamplified using the same two amplification primers which amplify the two adapter-modified target sequences. SEQ ID NO:12 is designed for use with the amplification primers of Multiplex System 1 and SEQ ID NO:26 is designed for use with the amplification primers of Multiplex System 2, i.e., with termini which hybridize to the target binding sequences of the selected amplification primers. The particular capture and detector probes listed in Table I are generally not critical, as alternative assay probes (e.g., the capture and detector probes) appropriate for detection of the internal control sequences as well as the 16S rDNA and IS6110 targets may be routinely designed using knowledge of the sequence to be detected.

The target binding sequences of the amplification primers and the adapter primers confer genus or species hybridization specificity and therefore provide the species- and genus -specificity to the assay. The target binding sequences are essential to obtain the species -specific/genus-specific multiplex amplification of the invention. By way of example, the IS6110 and 16S rDNA amplification primers listed above contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under optimum conditions. Similarly, the tail sequence of the amplification primer (5' to the restriction endonuclease recognition site) is generally not critical, although it is important to avoid including the restriction site used for SDA and to avoid sequences which will hybridize either to their own target binding sequence or to the other primers. The amplification primers of the invention therefore consist of the 3' target binding sequences indicated in Table I, a nickable restriction endonuclease recognition site 5' to the target binding sequence and a tail sequence about 10–25 nucleotides in length 5' to the restriction endonuclease recognition site. The length of the tail depends on the $T_m$ of the selected sequence, and can be easily adjusted by one skilled in the art to obtain sufficient hybridization. The amplification products of the IS6110, 16S rDNA and the internal control target sequences may be detected by hybridization to an oligonucleotide probe tagged with a detectable label, each target specifically hybridizing to a separately detectable probe. If the target-specific and control-specific probes are hybridized simultaneously to the amplification products, the labels should be separately identifiable to facilitate distinguishing the respective targets. Otherwise, separate aliquots of the amplification reaction may be hybridized to target -specific probes tagged with the same label. The detectable label may be conjugated to the probe after it is synthesized or it may be incorporated into the probe during synthesis, for example in the form of a label-derivatized nucleotide. Such labels are known in the art and include directly and indirectly detectable labels. Directly detectable labels produce a signal without further chemical reaction and include such labels as fluorochromes, radioisotopes and dyes. Indirectly detectable labels require further chemical reaction or addition of reagents to produce the detectable signal. These include, for example, enzymes such as horseradish peroxidase and alkaline phosphatase, ligands such as biotin which are detected by binding to label-conjugated avidin, and chemiluminescent molecules. The probes may be hybridized to their respective amplification products in solution, on gels, or on solid supports. Following hybridization, the signals from the associated labels are developed, detected and optionally quantitated using methods appropriate for the selected label and hybridization protocol. The amount of signal detected for each amplification product indicates the relative amount of each amplification product present.

An alternative method for detecting amplification products is by polymerase extension of a primer specifically hybridized to the target sequence. The primer is labeled as described above, for example with a radioisotope, so that the label of the primer is incorporated into the extended reaction product. This method is described in more detail by Walker, et al. (1992) Nuc. Acids Res. and PNAS, supra. Another method for detecting amplified target and control sequences is a chemiluminescent method in which amplified products are detected using a biotinylated capture oligodeoxynucleotide probe and an enzyme-conjugated detector oligodeoxynucleotide probe as described in U.S. Pat. No. 5,470,723. After hybridization of these two assay probes to different sites in the assay region of the target sequence, the complex is captured on a streptavidin-coated microtiter plate, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification. SDA reactions employing the primers of the invention may incorporate thymine as taught by Walker, et al., supra, or they may wholly or partially substitute 2'-deoxyuridine 5'-triphosphate for TTP in the reaction (as shown in the instant Examples) as a means for reducing cross-contamination of subsequent SDA reactions as taught in EP 0 624 643. dU (uridine) is incorporated into amplification products of both target and control sequences and can be excised by treatment with uracil DNA glycosylase (UDG). These abasic sites render the amplification product unamplifiable in subsequent SDA reactions. The internal control sequence as initially synthesized may also incorporate dU in place of thymine to prevent its amplification in subsequent SDAs. For example, SEQ ID NO:12 and SEQ ID NO:26 are shown in the attached Sequence Listing as containing thymine but may alternatively consist of the corresponding sequence in which thymine is replaced wholly or partially by dU. UDG may be inactivated by uracil DNA glycosylase inhibitor (Ugi) prior to performing the subsequent amplification to prevent excision of dU in newly-formed amplification products.

The primers and/or probes for performing the assay methods of the invention may be packaged in the form of a diagnostic kit for simultaneous genus-specific and species-specific amplification of mycobacterial DNA. The kits may comprise the amplification, adapter and bumper primers for genus-specific and species-specific amplification of mycobacterial DNA and, optionally, the reagents required for performing the SDA reaction (e.g., deoxynucleoside triphosphates, a nicking restriction enzyme, buffers, exo⁻ polymerase, etc.). The kits may further optionally include probes or primers useful for detecting or identifying the amplification products as described above, and/or an internal control sequence to be co-amplified with the *Mycobacterium* target sequences.

EXAMPLE 1

This experimental example demonstrates coamplification of genus- and species-specific target nucleic acids using the primers of Multiplex System 1. The following mycobacteria were tested: *M. tuberculosis, M. bovis* (CDC 81), *M. bovis-*

BCG, *M. africanum, M. avium, M. intracellulare, M. kansasii, M. gastri, M. fortuitum, M. paratuberculosis, M. chelonae, M. malmoense, M. szulgai, M. flavescens, M. xenopi, M. terrae, M. marinum, M. genovense, M. hemophilum* and *M. gordonae*. The non-mycobacterial organisms tested were: *Corynebacteria diphtheriae, Nocardia asteroides, Nocardia brasiliensis, Streptococcus albus, Actinomyces israelii, Rhodococcus equi* and *Propionibacterium acnes*.

SDA was performed generally as described in EP 0 684 315, substituting dUTP for TTP to allow removal of contaminating amplicons. The final concentrations of components in each 50 µL reaction were 27.5 mM $K_iPO_4$, pH 7.5, 6 mM MgOAc, 0.5 mM each dUTP, dGTP and dATP, 1.3 mM dCTPαS, 0.1 mg/mL acetylated BSA, 5% (v/v) dimethylsulfoxide, 8% (v/v) glycerol, 10 ng/µL human placental DNA, 1.6 units Bst polymerase (exo⁻ klenow fragment, New England BioLabs), 160 units BsoBI (New England Biolabs, Beverly, Mass.), and 0, 1, 10, 100 or $10^6$ genomes of the organism being tested. *M. tuberculosis* was tested at 0, 1, 10 and 100 genomes. The other M.tb complex species and non-M.tb complex mycobacteria were tested at 100 genomes. Non-mycobacterial organisms were tested at $10^6$ genomes. The reactions also contained 25 copies of an internal amplification control sequence (tSig1 - SEQ ID NO:12). Each sample further contained eight primers, as follows: 0.5 µM each of amplification primers GS1.3 (SEQ ID NO:1) and BisS1.1 (SEQ ID NO:2); 50 nM each of adapter primers AG1A (SEQ ID NO:3) and Bso-G Atb1 (SEQ ID NO:6); 25 nM each of bumper primers Bso-G BG1 (SEQ ID NO:8), Bso-G BG2 (SEQ ID NO:9), Mtb 37 (SEQ ID NO:10) and Mtb48 (SEQ ID NO: 11). The bumper primers used in this experiment are not critical to achieve genus/species multiplex amplification. They hybridize upstream of the amplification and adapter primers and, when extended, function to displace the extension products of the amplification and adapter primers. Other bumper primers which hybridize upstream at a position sufficiently close to an amplification or adapter primer to displace it by extension of the bumper primer may be routinely designed using knowledge of the IS6110 and 16S rDNA sequences. Each reaction was assembled to contain all reagents except Bst and BsoBI, using concentrated stock solutions of each reagent. The samples were then heated for 2 min. at 95° C to denature the DNA and transferred to a 52° C water bath for 3–5 min. The enzymes were added for a total sample volume of 50 µL, and the samples were incubated for 30 min. at 52° C to allow amplification to proceed. Amplification was terminated by placing the reactions in a boiling water bath for 2–3 min.

The amplification products were analyzed using the chemiluminescent assay described in U.S. Pat. No. 5,470,723, substituting TG-01B3(SEQ ID NO:13) for the 16S capture probe of that assay. The remaining capture and detector probes were those described in Example 3 of U.S. Pat. No. 5,470,723 (identified herein as SEQ ID NOs:14, 15, 16, 17 and 18). RLU values greater than 100 were interpreted as positive for target amplification. The IS6110 target was amplified only in members of the *M. tuberculosis* complex (*M. tuberculosis, M. bovis, M. africanum, M. bovis-BCG*) and amplification was detected when as few as one initial genome copy was present in the reaction. Although *M. microti* was not tested, it has the same IS6110 target sequence as the other species and would be expected to produce the same result. In contrast, positive 16S rDNA target amplification was observed for all members of the genus *Mycobacterium* except *M. terrae, M. genovense* and *M. xenopi*. The 16S amplification signal was generally not positive at one genome, however, the signal intensity became strongly positive as the initial genome number increased to 10–100 genomes. The apparent discrepancy between amplification of the two targets is probably due to the fact that a single *M. tuberculosis* genome contains about 10 copies of IS6110, whereas each mycobacterial genome contains only 1–2 copies of the 16S rDNA target.

None of the closely related non-mycobacterial genera tested were positive for amplification of either target except *Nocardia asteroides*, which gave a weakly positive signal for 16S rDNA at $10^6$ genomes (123 RLU). This is in contrast to a typical RLU >2000 for ten 16S rDNA targets in *M. tuberculosis*. The genus-specific primers of the invention therefore show no appreciable cross-reactivity with non-mycobacterial DNA. Strong internal control signals were also observed in all amplification reactions, confirming amplification efficacy even in the absence of both IS6110 and 16S signals. These experiments demonstrate that this primer set performs in multiplex tSDA to simultaneously amplify a target sequence found in most clinically relevant mycobacteria and a target sequence which is indicative of a species of the *M. tuberculosis* complex.

EXAMPLE 2

This experimental example demonstrates coamplification of genus and species-specific targets using Multiplex System 2. IS61 10 and 16S rDNA targets were amplified from the genomic DNA of *M. tuberculosis* and *M. bovis-BCG* essentially as described in Example 1, substituting 30 mM potassium phosphate and 7 mM magnesium acetate, and the using the following primers: 0.5 µM each amnplification primers GS1.3 (SEQ ID NO:1)and BisS2.2 (SEQ ID NO:19); 50 nM each adapter primers G1T1A and T2G2A (SEQ ID NO:20); 25 nM each bumper primers Bso-G BG1 (SEQ ID NO:8), Bso-G BG2 (SEQ ID NO:9), Mtb 37 (SEQ ID NO:10) and Mtb 48 (SEQ ID NO:11). No internal control was present in these experiments, but internal control sequences as described herein may be added and coamplified. Ten or 100 initial target genomes were present in the reaction and a negative control was run which contained no target DNA. Amplification products were analyzed as in Example 1, substituting GCAP-2 (SEQ ID NO:22) as the capture probe.

In both species, positive signals were obtained for IS6110 and 16S rDNA targets with as few as 10 initial copies of genomic DNA. Because it is the target binding sequence which confers target specificity on the primer, it would be expected that the genus- and species-specificity of the primers used in this experiment would be the same as the primers of Example 1, as the target binding sequences are the same.

What is claimed is:

1. An oligonucleotide consisting of a target binding sequence selected from the group consisting of the target binding sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:23, SEQ ID NO:24, SEQ ID NO:25, SEQ ID NO:20, SEQ ID NO:21 and SEQ ID NO:27 and, optionally, a sequence required for an amplification reaction or an adapter sequence.

2. The oligonucleotide of claim 1 wherein the sequence required for the amplification reaction is a restriction endonuclease recognition site which is nicked by a restriction endonuclease during Strand Displacement Amplification.

3. The oligonucleotide of claim 1 selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:23, SEQ ID NO:24, SEQ ID NO:25, SEQ ID NO:19, SEQ ID NO:20, SEQ ID NO:21 and SEQ ID NO:27.

4. An oligonucleotide selected from the group consisting of SEQ ID NO:12, SEQ ID NO:13, SEQ ID NO:22 and SEQ ID NO:26.

5. A method for simultaneously amplifying a first and a second target comprising:

a) hybridizing a first amplification primer to the first target, the first amplification primer comprising the target binding sequence of SEQ ID NO:1 and a recognition site for a restriction endonuclease which nicks one strand of a double-stranded hemimodified recognition site for the restriction endonuclease, extending the first amplification primer to produce a first extension product and displacing the first extension product;

b) hybridizing to the first extension product a first adapter primer consisting of a target binding sequence selected from the group consisting of the target binding sequences of SEQ ID NO:3, SEQ ID NO:4, SEQ ID NO:5 and SEQ ID NO:27, and a first adapter sequence substantially identical to the target binding sequence of SEQ ID NO:2, extending the first adapter primer to produce a second extension product and displacing the second extension product;

c) hybridizing a second amplification primer to the second target, the second amplification primer comprising the target binding sequence of SEQ ID NO:2 and the recognition site for the restriction endonuclease, extending the second amplification primer to produce a third extension product and displacing the third extension product;

d) hybridizing to the third extension product a second adapter primer consisting of a target binding sequence selected from the group consisting of the target binding sequences of SEQ ID NO:6, SEQ ID NO:7, SEQ ID NO:23, SEQ ID NO:24 and SEQ ID NO:25 and a second adapter sequence substantially identical to the target binding sequence of SEQ ID NO:1, extending the second adapter primer to produce a fourth extension product, displacing the fourth extension product, and;

e) si multaneously amplifying the second and fourth extension products using the first and second amplification primers.

6. The method of claim 5 wherein:

a) the first amplification primer consists of SEQ ID NO:1;

b) the first adapter primer consists of SEQ ID NO:3, SEQ ID NO:4, SEQ ID NO:5 or SEQ ID NO:27;
c) the second amplification primer consists of SEQ ID NO:2, and;
d) the second adapter primer consists of SEQ ID NO:6, SEQ ID NO:7, SEQ ID NO:23, SEQ ID NO:24 or SEQ ID NO:25.

7. The method o f claim 5 further comprising detecting the amplified first or second target.

8. The method of claim 7 where in the amplified first target is detected using SEQ ID NO:13 and SEQ ID NO:14.

9. The method of claim 7 wherein the amplified second target is detected using SEQ ID NO:15 and SEQ ID NO:16.

10. The method of claim 5 further comprising coamplifying an internal control sequence consisting of SEQ ID NO:12, or SEQ ID NO:12 in which thymine has been wholly or partially substituted with uridine, and detecting the amplified internal control sequence.

11. The method of claim 10 wherein the amplified internal control sequence is detected using SEQ ID NO:1 7 and SEQ ID NO:18.

12. A method for simultaneously amplifying a first and a second target comprising: a) hybridizing a first amplification primer to the first target, the first amplification primer comprising the target binding sequence of SEQ ID NO:1 and a recognition site for a restriction endonuclease which nicks one strand of a double-stranded hemimodified recognition site for the restriction endonuclease, extending the first amplification primer to produce a first extension product and displacing the first extension product;
b) hybridizing to the first extension product a first adapter primer consisting of a target binding sequence of SEQ ID NO:20 and a first adapter sequence substantially identical to the target binding sequence of SEQ ID NO:19, extending the first adapter primer to produce a second extension product and displacing the second extension product;
c) hybridizing a second amplification primer to the second target, the second amplification primer comprising the target binding sequence of SEQ ID NO:19 and the recognition site for the restriction endonuclease, extending the second amplification primer to produce a third extension product and displacing the third extension product;
d) hybridizing to the third extension product a second adapter primer consisting of the target binding sequence of SEQ ID NO:21 and a second adapter sequence substantially identical to the target binding sequence of SEQ ID NO:1, extending the second adapter primer to produce a fourth extension product, displacing the fourth extension product, and;
e) simultaneously amplifying the second and fourth extension products using the first and second amplification primers.

13. The method of claim 12 wherein:
a) the first amplification primer consists of SEQ ID NO:1;
b) the first adapter primer consists of SEQ ID NO:20;
c) the second amplification primer consists of SEQ ID NO:19, and;
d) the second adapter primer consists of SEQ ID NO:2 1.

14. The method of claim 12 further comprising detecting the amplified first or second target.

15. The method of claim 14 wherein the first amplified target is detected using SEQ ID NO:22 and SEQ ID NO:14.

16. The method of claim 14 wherein the second amplified target is detected using SEQ ID NO:15 and SEQ ID NO:16.

17. The method of claim 12 further comprising coamplifying an internal control sequence consisting of SEQ ID NO:26, or SEQ ID NO:26 in which thymine has been wholly or partially substituted with uridine, and detecting the amplified internal control sequence.

18. A method for simultaneously amplifying a first and a second target comprising:
a) hybridizing a first amplification primer to the first target, the first amplification primer comprising a target binding sequence selected from the group consisting of the target binding sequences of SEQ ID NO:3, SEQ ID NO:4, SEQ ID NO:5 and SEQ ID NO:27 and a recognition site for a restriction endonuclease which nicks one strand of a double-stranded hemimodified recognition site for the restriction endonuclease, extending the first amplification primer to produce a first extension product and displacing the first extension product;
b) hybridizing to the first extension product a first adapter primer consisting of the target binding sequence of SEQ ID NO:1, and a first adapter sequence substantially identical to the target binding sequence of SEQ ID NO:2, extending the first adapter primer to produce a second extension product and displacing the second extension product;
c) hybridizing a second amplification primer to the second target, the second amplification primer comprising a target binding sequence selected from the group consisting of the target binding sequences of SEQ ID NO:6, SEQ ID NO:7, SEQ ID NO:23, SEQ ID NO:24 and SEQ ID NO:25 and the recognition site for the restriction endonuclease, extending the second amplification primer to produce a third extension product and displacing the third extension product;
d) hybridizing to the third extension product a second adapter primer consisting of the target binding sequence of SEQ ID NO:2 and a second adapter sequence substantially identical to the target binding sequence of SEQ ID NO:1, extending the second adapter primer to produce a fourth extension product, displacing the fourth extension product, and;
e) simultaneously amplifying the second and fourth extension products using the first and second amplification primers.

19. A method for simultaneously amplifying a first and a second target comprising:
a) hybridizing a first amplification primer to the first target, the first amplification primer comprising the target binding sequence of SEQ ID NO:20 and a recognition site for a restriction endonuclease which nicks one strand of a double-stranded hemimodified recognition site for the restriction endonuclease, extending the first amplification primer to produce a first extension product and displacing the first extension product;
b) hybridizing to the first extension product a first adapter primer consisting of a target binding sequence of SEQ ID NO:1 and a first adapter sequence substantially identical to the target binding sequence of SEQ ID NO:19, extending the first adapter primer to produce a second extension product and displacing the second extension product;
c) hybridizing a second amplification primer to the second target, the second amplification primer comprising the target binding sequence of SEQ ID NO:21 and the recognition site for the restriction endonuclease, extending the second amplification primer to produce a third extension product and displacing the third extension product;

d) hybridizing to the third extension product a second adapter primer consisting of the target binding sequence of SEQ ID NO:19 and a second adapter sequence substantially identical to the target binding sequence of SEQ ID NO:1, extending the second adapter primer to produce a fourth extension product, displacing the fourth extension product, and;

e) simultaneously amplifying the second and fourth extension products using the first and second amplification primers.

* * * * *